(12) United States Patent
Goodson

(10) Patent No.: US 9,398,973 B1
(45) Date of Patent: Jul. 26, 2016

(54) ABDOMINAL SPLINT AND BACK SUPPORT WRAP

(76) Inventor: Celeste Emory Goodson, Irvine, CA (US)

(*) Notice: Subject to any disclaimer, the term of this patent is extended or adjusted under 35 U.S.C. 154(b) by 294 days.

(21) Appl. No.: 13/486,733

(22) Filed: Jun. 1, 2012

Related U.S. Application Data

(60) Provisional application No. 61/519,905, filed on Jun. 1, 2011.

(51) Int. Cl.
*A61F 5/02* (2006.01)

(52) U.S. Cl.
CPC ...................... *A61F 5/028* (2013.01)

(58) Field of Classification Search
USPC ............. 602/19–20, 2, 32, 36, 60–61, 67, 70; 128/99.1, 96.1, 100.1, 101.1, 106.1, 128/107.1, 109.1, 869–870, 873–876; 450/154–155; 2/310–311, 44
See application file for complete search history.

(56) References Cited

U.S. PATENT DOCUMENTS

| | | | | |
|---|---|---|---|---|
| 3,598,114 A * | 8/1971 | Lewis | ................... | A61F 13/148 602/19 |
| 4,195,640 A * | 4/1980 | Castiglia | ..................... | 450/155 |
| 4,746,318 A | 5/1988 | Moyer | | |
| 4,761,324 A * | 8/1988 | Rautenberg | ............ | A41D 31/02 428/198 |
| 4,789,372 A | 12/1988 | Wicks | | |
| 4,976,653 A | 12/1990 | White | | |
| 5,189,736 A | 3/1993 | Price | | |
| 5,407,422 A * | 4/1995 | Matthijs et al. | ................. | 602/19 |
| 5,548,843 A * | 8/1996 | Chase | ................ | A41D 13/0525 2/102 |
| 5,810,699 A * | 9/1998 | Nadeau | ................ | A63B 21/065 182/105 |
| D404,490 S | 1/1999 | Tripolsky | | |
| 5,915,531 A | 6/1999 | Hilpert et al. | | |
| 6,194,629 B1 * | 2/2001 | Bernhard | ............ | A61F 13/0273 128/882 |
| 7,160,262 B2 * | 1/2007 | Wicks | ...................... | A41C 1/08 602/19 |
| 8,057,417 B2 * | 11/2011 | Imai | ................................ | 602/19 |
| 8,105,256 B1 * | 1/2012 | Ariza | ................................ | 602/19 |
| 2007/0232973 A1 * | 10/2007 | Serola | ............................. | 602/19 |

OTHER PUBLICATIONS

Diastasis Rehab—The Tupler Technique for Treating a Diastasis Recti. Printed Sep. 4, 2012. "Diastasis Rehab Splint." (http://www.diastasisrehab.com/diastore/product_info.php?cPath=1_7&products_id=68) 2 pages.

* cited by examiner

*Primary Examiner* — Ophelia A Hawthorne
(74) *Attorney, Agent, or Firm* — Vorys, Sater, Seymour and Pease LLP

(57) ABSTRACT

Disclosed is a abdominal splinting device to stabilize and support a woman's abdomen during pregnancy and to be used in treatment of diastasis recti in postnatal women. The abdominal splinting device has a back support panel with a central region and opposing first and second side regions, and arms extending from the side regions, where the arms each have a length sufficient to contact the opposite side region when wrapped about a human's trunk region. Also disclosed is a method of treating diastasis recti using the abdominal splinting device. The method includes the steps of providing a abdominal splinting device, centering the abdominal splinting device about a user's torso, applying manual traction to the user's rectus abdominis to bring the two opposing halves of the rectus abdominis near to each other, affixing the arms to the back support panel, and instructing the user to perform abdominal strengthening exercises.

19 Claims, 6 Drawing Sheets

ABDOMINAL SPLINT AND BACK SUPPORT WRAP

CROSS-REFERENCE TO RELATED APPLICATIONS

This U.S. patent application claims priority to and the benefit of Provisional U.S. Patent Application Ser. No. 61/519,905 filed on Jun. 1, 2011, which is incorporated by reference herein in its entirety.

BACKGROUND

Splints of many types are known in the medical community and are used to stabilize and support various body parts. Some splints are used to immobilize broken bones while others are used to support musculature and minimize repetitive strain injuries.

Pregnant women may find that they benefit from placing a splint around their abdomen as the pregnancy progresses. Unsupported, the weight of the abdomen of a pregnant woman may cause back pain as the back supports the additional weight of the growing abdomen. Further, the additional weight of the abdomen may cause the woman to feel unsupported and uncomfortable as she performs moderate or strenuous exercise. If a woman places a splint around her abdomen, she may find that the support reduces back pain and increases her level of comfort as she continues an exercise regimen.

An additional side effect that may occur during pregnancy is diastasis recti, the separation of the rectus abdominis muscle, or the "six pack" muscle of a woman's abdomen. Diastasis recti occurs when the size of the growing fetus stretches both the linea alba, the connecting tissue running longitudinally through the rectus abdominis, and the rectus abdominis muscle. The stretching and subsequent thinning of the linea alba and rectus abdominis causes the halves of the rectus abdominis muscle to linearly stretch outwards from each other, causing what appears to be a small separation in the rectus abdiminis at the midline of the body. Some degree of abdominal separation during pregnancy is typical, and the degree of separation varies among different women. Although some women spontaneously heal the diastasis recti within six to eight weeks after giving birth, not all women heal spontaneously. To facilitate the healing process, women who do not heal the diastasis recti spontaneously may benefit from wearing a splint and completing abdominal strengthening exercises post-partum. An abdominal splinting device that provides manual traction, temporarily closing the separation of the rectus abdominus halves, can facilitate healing of the diastasis. Further, a splint which provides even, simultaneous traction along both sides of the diastasis is particularly helpful as it more closely mimics the natural alignment of the musculature and properly centers the halves along the woman's midline.

Previous abdominal support systems have been designed to either support the abdomen of a pregnant woman or to provide splinting of the abdomen of postnatal women. This invention provides a splint which may be worn during pregnancy to support, splint, and stabilize the abdomen, and which may also be may be worn by postnatal women to splint the rectus abdominis muscle for treatment of a diastasis recti.

SUMMARY

In one embodiment, an abdominal splinting device is described, the device having a back support panel having an inner and outer surface, a central region and opposing first and second side regions; an arm extending outward from each of the first and second side regions, each arm having a width less than any width of the back support panel and further having a length sufficient to contact the opposite side region; the first and second side regions each having a mating zone on their outer surfaces for receiving the arm extending from the opposite side region when the abdominal splinting device is wrapped around a human's trunk region; and each arm having a means for attaching the arm to the opposing side region mating zone.

In a second embodiment, an abdominal splinting device is described, the device having a back support panel having an inner and outer surface, a central region and opposing first and second side regions; an arm extending outward from each of the first and second side regions, each arm having a width less than any width of the back support panel and further having a length sufficient to contact the opposite side region; the first and second side regions each having a mating zone on their outer surfaces for receiving the arm extending from the opposite side region when the abdominal splinting device is wrapped around a human's trunk region; and each arm terminating in a series of hooks attached an inner surface of the arm.

A therapeutic method of treating diastasis recti is described, the method having the steps of providing a abdominal splinting device having inner and outer surfaces, a back support panel, and first and second arms extending outward from each of first and second side regions of the back support panel, wherein the arms have means for attaching the arms to the back support panel affixed to the inner surface of the arms; centering the abdominal splinting device about a user's torso; applying manual traction to the user's rectus abdominis to bring two opposing halves of the rectus abdominis near to each other; crossing the first arm over the user's torso and affixing the first arm to the outer surface of the back support panel using the attaching means while simultaneously crossing the second arm over the user's torso and affixing the second arm to the outer surface of the back support panel using the attaching means; and instructing the user to perform abdominal strengthening exercises.

DETAILED DESCRIPTION

Figure 1:
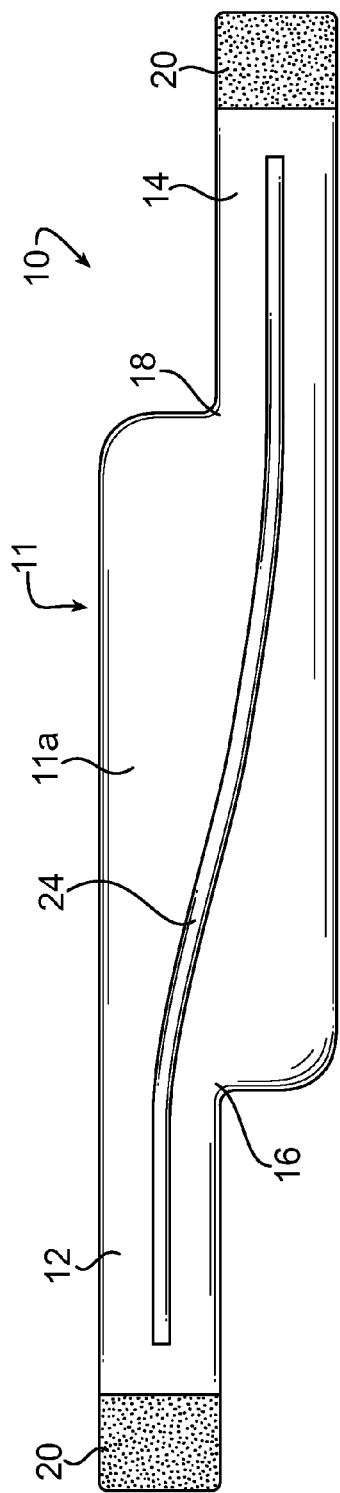
FIG. 1 is a top plan view of an inner surface of the abdominal splinting device.

FIG. 1 shows a top plan view of an inner surface of the abdominal splinting device 10. FIG. 1 shows the inner surface of the abdominal splinting device 10 that is worn against the body when the abdominal splinting device is in use. As shown, the device has a back support panel 11 with a central region 11a, a first side region 16, and a second side region 18. In one embodiment, back support panel 11 is generally rectangular in shape, while in other embodiments it may be square or irregularly shaped. In some embodiments, back support panel 11 may feature stays to further shape and support the back support panel 11. Regardless of its shape, back support panel 11, particularly opposing first side region 16 and second side region 18, serves as an anchor for first arm 12 and second arm 14 of the abdominal splinting device 10, discussed below, and serves as support for the user's lower back, also discussed below. Because the abdominal splinting device 10 may be manufactured in variable sizes, back support panel 11 may have variable dimensions. However, back support panel 11 is generally sized to approximate the dimensions of the user's lower back. In an alternate embodiment, back support panel may feature one or more pocket folds, elastic bands, or buckles to make the size of the back support panel adjustable.

With continued reference to FIG. 1, the abdominal splinting device 10 has two arms, a first arm 12 and a second arm 14. First arm 12 extends from first side region 16 of the back support panel, and second arm 14 extends from second side region 18 of the back support panel. Both first arm 12 and the second arm 14 extend outward from the back support panel 11. However, the position of the first arm 12 on the first side region 16 is staggered relative to the position of the second arm 14 on the second side region 18. Because the first and second arms extend from offset positions, first arm 12 extends in a generally parallel, non-overlapping fashion relative to the second arm 14.

First arm 12 and second arm 14 may have variable lengths. In a first embodiment, first arm 12 and second arm 14 are of equal length. In a second embodiment, first arm 12 and second arm 14 may be of unequal lengths. In some embodiments, first arm 12 and second arm 14 may be longer than back support panel 11, while in other embodiments first arm 12 and second arm 14 may be shorter than back support panel 11. Further, first arm 12 and second arm 14 may feature one or more pocket folds, elastic bands, or buckles to make the length of the arms adjustable.

In addition to variable lengths, first arm 12 and second arm 14 may have variable widths. In a first embodiment, first arm 12 and second arm 14 are of equal widths, while in a second embodiment they may be of unequal widths. Regardless of whether the widths of first arm 12 and second arm 14 are equal or unequal, each individual arm has a width less than the width of the back support panel 11.

Figure 5:
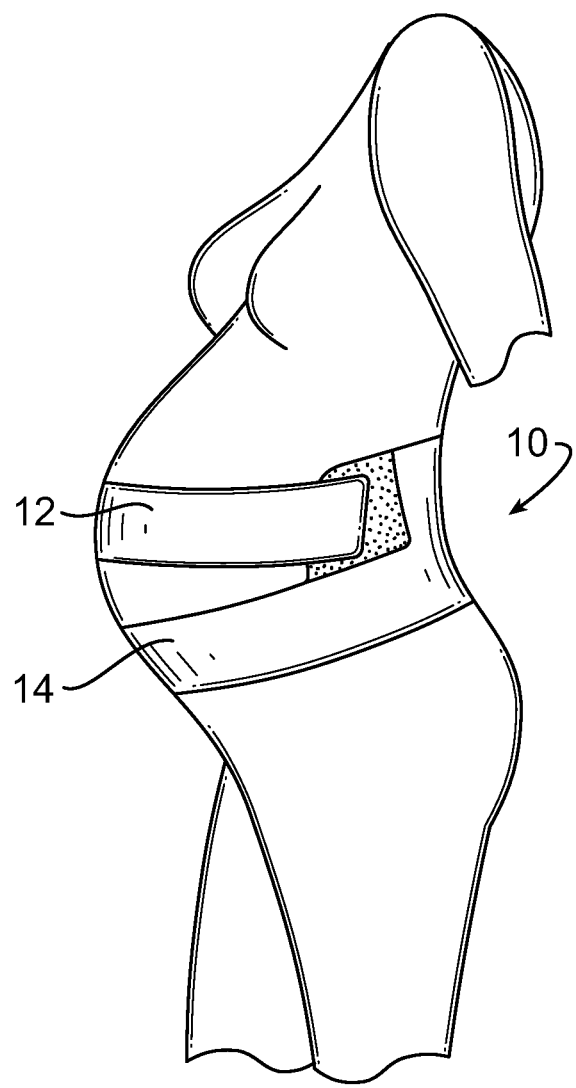
FIG. 5 is a side view of a pregnant woman wearing the abdominal splinting device in a second arrangement in accordance with one embodiment of the invention.
Figure 6:
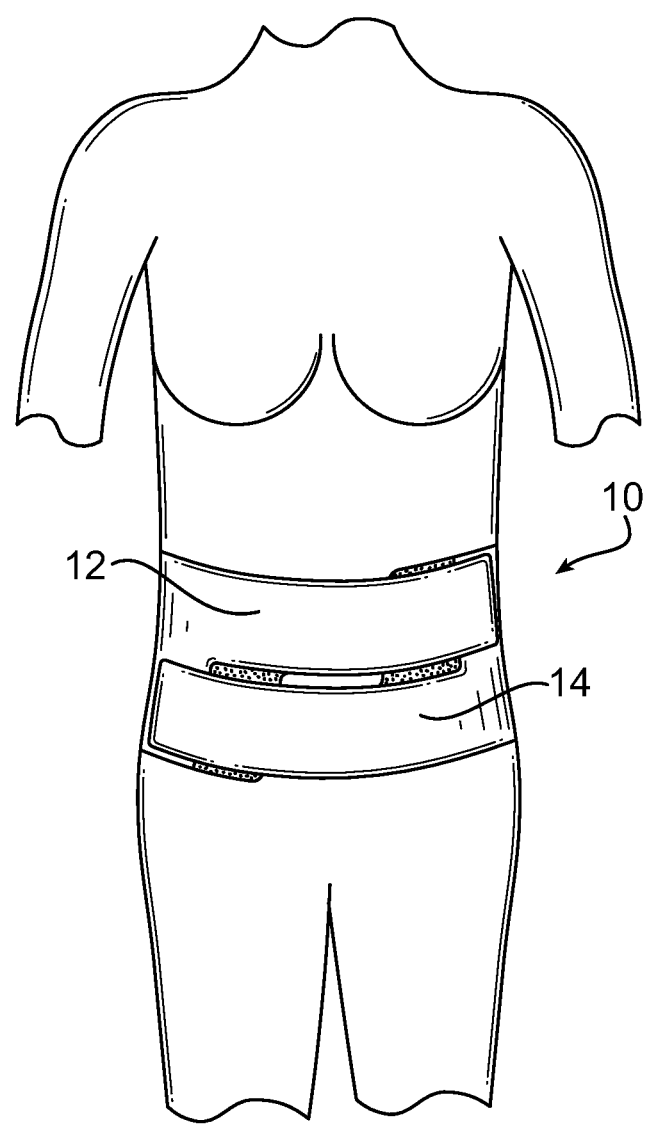
FIG. 6 is a front view of a postnatal woman wearing the abdominal splinting device in accordance with one embodiment of the invention.
Figure 7:
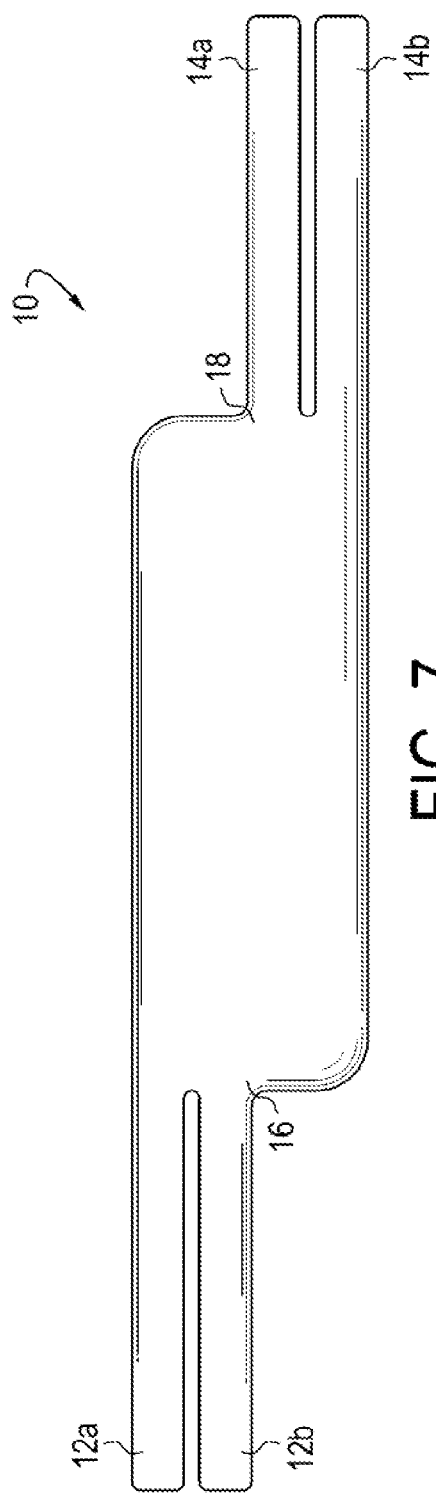
FIG. 7 is a top plan view of the abdominal splinting device having multiple arms.

While FIGS. 1 through 6 show the abdominal splinting device 10 having first and second arms, 12 and 14, respectively, the abdominal splinting device 10 may have more than two arms as depicted in FIG. 7. In alternate embodiments, the abdominal splinting device 10 may have three or more arms. For example, two or more arms 12a and 12b may extend from first side region 16, and/or two or more arms 14a and 14b may extend from second side region 18 without departing from the spirit of the invention.

First arm 12 and second arm 14 terminate in an attachment mechanism 20. In one embodiment, attachment mechanism 20 may be part of a hook and loop system similar to a VELCRO® fastening system. In other embodiments, attachment mechanism 20 may be part of a hook and eye system, a button system, or a snap system. In yet another embodiments, attachment mechanism 20 may be an adhesive. In still other embodiments, other means for fastening first arm 12 and second arm 14 to the back support panel 11 may be used without departing from the intent of the invention.

Figure 2:
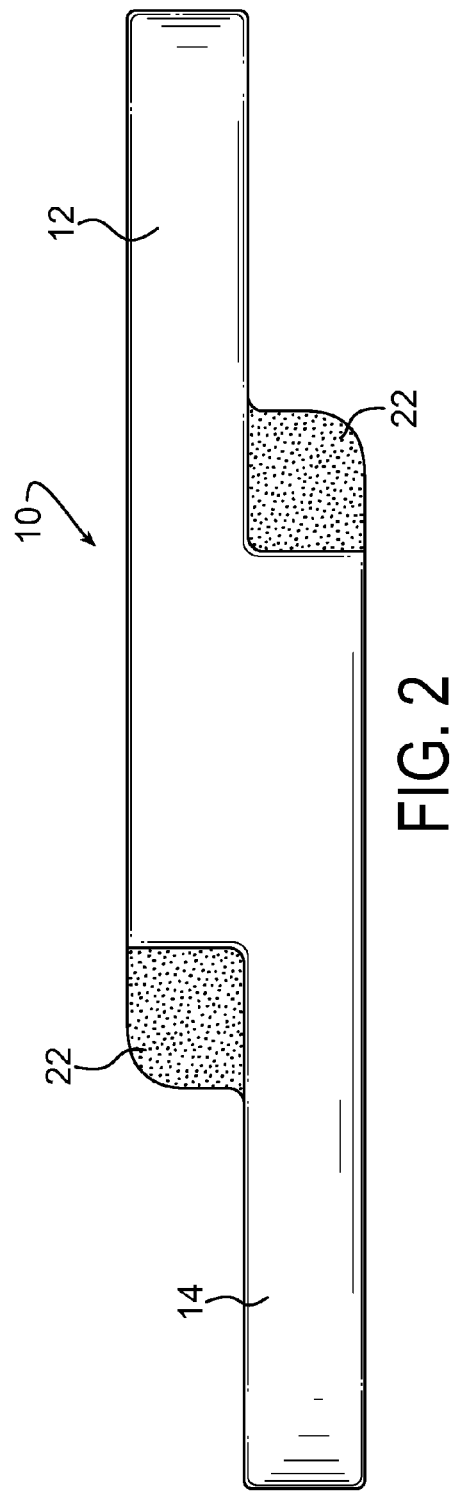
FIG. 2 is a top plan view of an outer surface of the abdominal splinting device.

FIG. 2 shows a top plan view of an outer surface of the abdominal splinting device 10. The attachment mechanism 20 connects to a mating zone 22 located to the outer surface of the abdominal splinting device 10. Mating zone 22 contains the corresponding part of the fastening system used in attachment mechanism 20. In an embodiment where a VELCRO® fastening system is used, for example, attachment mechanism 20 may be comprised of hooks and mating zone 22 may be comprised of loops of fabric to mate with the hooks. Because the abdominal splinting device 10 is intended to accommodate users of variable sizes and to accommodate users in various states of pregnancy, mating zone 22 may be variably sized. Further, to accommodate different sizes of users or different states of pregnancy, the number of fastening members in the attachment mechanism 20 may be smaller than the number of fastening members used in the mating zone 22. For example, where the fastening system is a snap system, attachment mechanism 20 may feature a smaller number of half snaps than the number featured in the mating zone 22.

Still referring to FIG. 1, in one embodiment a portion of non-slip material 24 may be affixed to the inner surface of the abdominal splinting device 10. The non-slip material functions to provide traction against a user's skin or base layer of fabric to prevent the abdominal splinting device 10 from shifting or twisting about the user's torso and to keep the abdominal splinting device 10 properly positioned on the user's torso. In alternate embodiments, the abdominal splinting device 10 may not feature the non-slip material.

Figure 8:
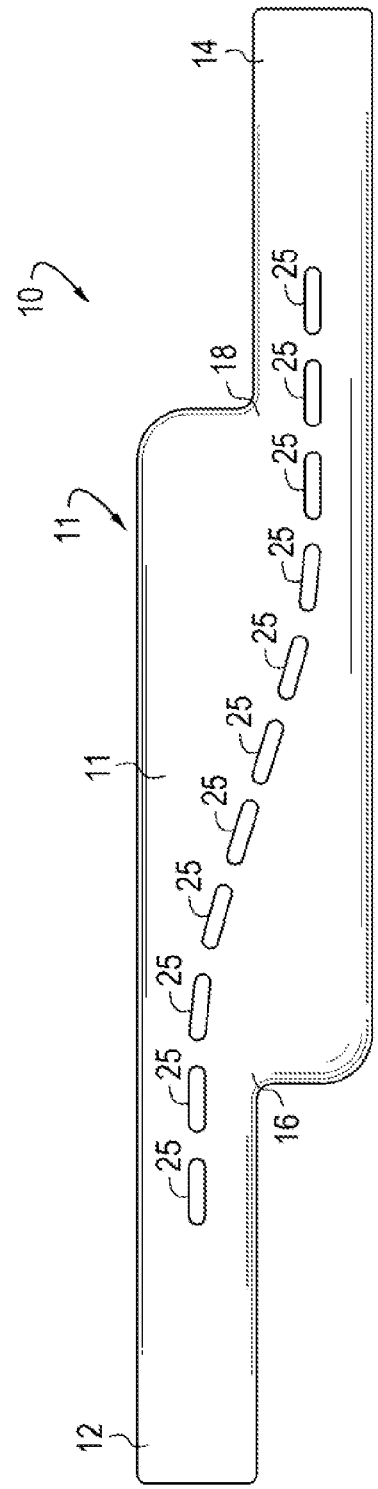
FIG. 8 is a top plan view of an inner surface of the abdominal splinting device.

Returning now to embodiments where the non-slip material is affixed to the abdominal splinting device 10, in a first embodiment the non-slip material 24 may be affixed to the back support panel of the abdominal splinting device 10. In another embodiment, the non-slip material 24 may be affixed to one or both of the arms of the abdominal splinting device 10. In yet another embodiment, the non-slip material 24 may be affixed to the back support panel and the arms of the abdominal splinting device 10. In one embodiment, the non-slip material may be a single piece affixed to the abdominal splinting device 10. In another embodiment, the non-slip material may be multiple pieces 25 affixed to the abdominal splinting device 10 as exemplified by FIG. 8; however, FIG. 8 should not be construed as limiting the size, shape, or configuration of the multiple pieces of non-slip material 25. The non-slip material 24 may be any reasonable size: in one embodiment, the non-slip material 24 may be substantially smaller than the abdominal splinting device 10, while in other embodiments the non-slip material 24 may be substantially the same size as the abdominal splinting device 24.

In one embodiment, the non-slip material may be comprised of rubber or a rubber blend. In another embodiment, the non-slip material may be comprised of nylon or a nylon blend. In yet another embodiment, the non-slip material may be comprised of silicon or a silicon blend. In still other embodiments, the non-slip material may be comprised of other polymers or polymeric blends without departing from the intent of the invention. By way of a non-limiting example, neoprene may be used as the non-slip material affixed to the abdominal splinting device.

As shown in FIG. 1, the abdominal splinting device 10 may be comprised of one continuous piece of material. In alternate embodiments, the abdominal splinting device 10 may be comprised of multiple pieces of material. For example, back support panel 11 and first arm 12 and second arm 14 may all be comprised of individual pieces of material and then attached to each other. If the abdominal splinting device 10 is comprised of multiple pieces of material, the pieces may be attached to each other by any suitable means including, for example, sewing or adhesive.

The abdominal splinting device 10 may be comprised of a fabric material. In one embodiment, the abdominal splinting device 10 may be comprised of an elastic, breathable fabric material. In some embodiments, this elastic, breathable fabric material may be comprised of cotton yarns, polyester, elasthane, or other polymeric yarns, and latex-free elastic yarns. In accordance with this embodiment, for example, the abdominal splinting device 10 may be comprised of cotton and polyester, or cotton and elasthane. In alternate embodiments, this elastic, breathable fabric material may be comprised of cotton yarns, polyester, elasthane, or other polymeric yarns, and latex-based elastic yarns. In still other alternate embodiments, this elastic, breathable fabric material may be comprised in part of bamboo based yarns.

In one embodiment, the abdominal splinting device 10 may be worn close to a user's skin as a type of undergarment. In an alternate embodiment, the abdominal splinting device 10 may be worn over a base layer of clothing.

Figure 3:
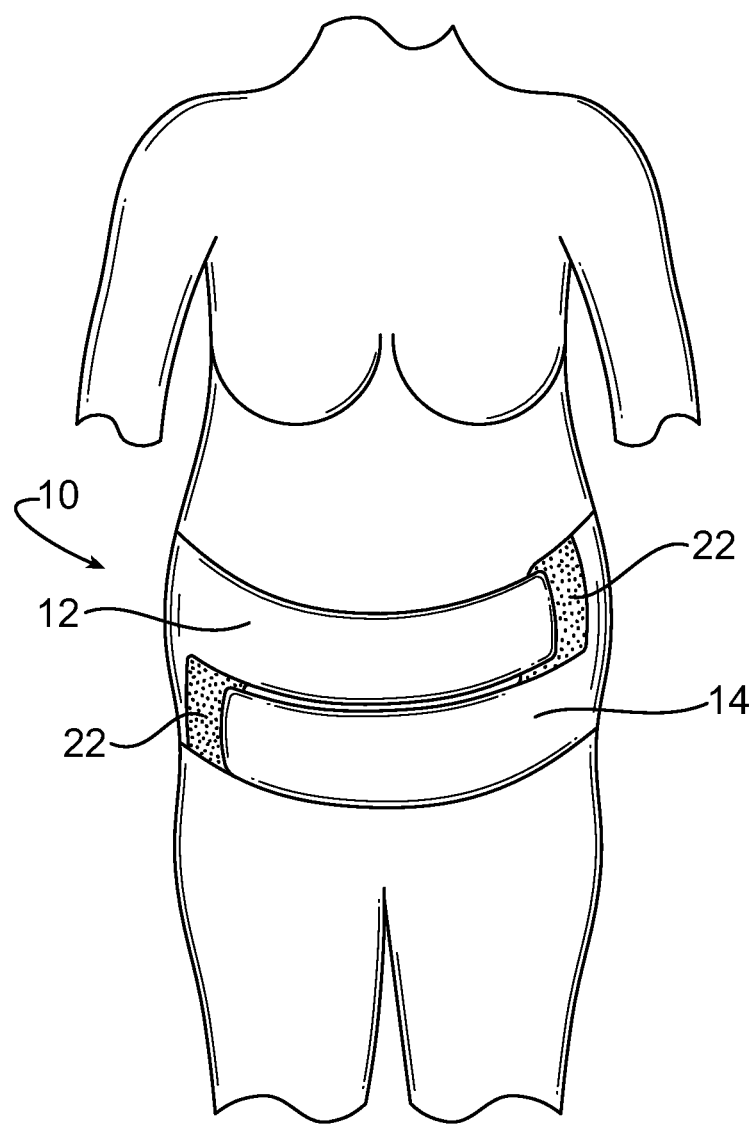
FIG. 3 is a front view of a pregnant woman wearing the abdominal splinting device in accordance with one embodiment of the invention.

Turning now to FIG. 3, the abdominal splinting device 10 may be worn by pregnant women. In this embodiment, the abdominal splinting device 10 is designed to support the back and abdomen of the pregnant women while providing a comfortable fit. As seen in FIG. 3, the arms 12 and 14 of the abdominal splinting device 10 are worn parallel about the body. The woman arranges the device so that the inner surface of the abdominal splinting device, the side with the non-slip material, will be worn next to the body, and centers the back support panel about her back. Then, she places one of the arms 12 or 14 in one hand, and the other of arms 12 and 14 in her other hand. To facilitate simultaneous positioning of the arms 12 and 14, the user may choose to use her right hand to grab the arm from the left side of her body, and her left hand to grab the arm from the right side of her body. She wraps the arms about her body, and affixes the first arm 12 and second arm 14 to the back support panel via the attachment mechanism 22. As seen in FIG. 3, the straps are worn substantially parallel about the body; it is preferred that arms 12 and 14 do not cross over each other. Further, because the straps are offset, they do not overlap and the abdominal splinting device 10 does not create an excess of fabric about the woman's abdomen, making the abdominal splinting device comfortable to wear. However, in some embodiments, the widths of first arm 12 and second arm 14 may be sufficient to cause the arms to overlap without departing from the spirit of the invention. Finally, because the abdominal splinting device 10 features non-slip material, the splint does not twist about the torso or move to a different location on the torso while the woman is wearing the abdominal splinting device 10.

Figure 4:
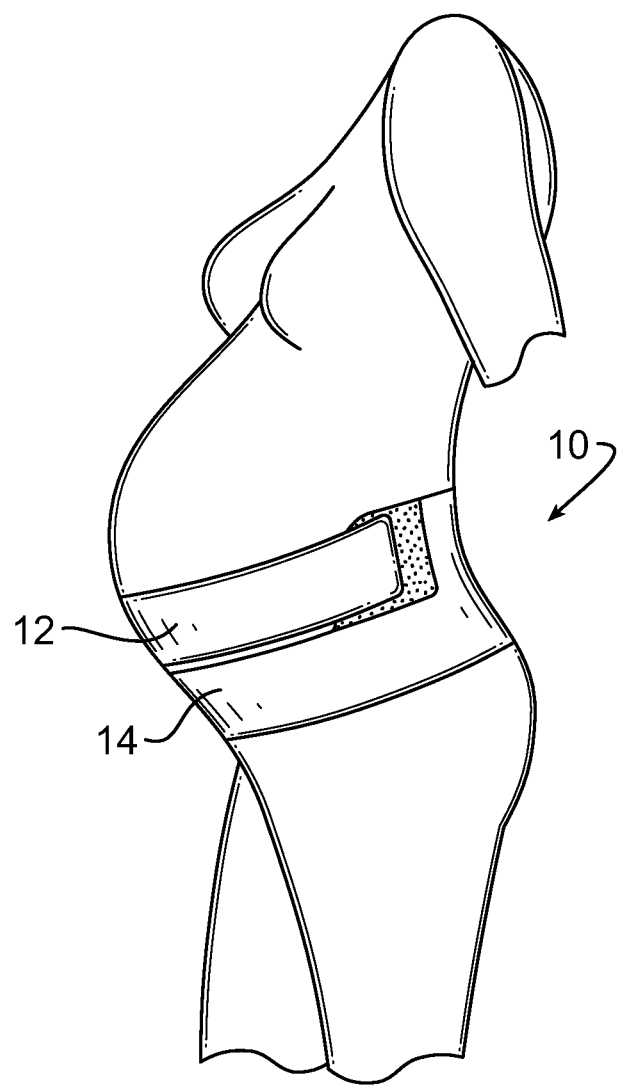
FIG. 4 is a side view of a pregnant woman wearing the abdominal splinting device in a first arrangement in accordance with one embodiment of the invention.

FIG. 4 shows the abdominal splinting device 10 worn by a pregnant woman in a first arrangement in accordance with the method of placement described above. In this arrangement, first arm 12 and second arm 14 are worn near the lower portion of the abdomen, at or below the belly button, with arms 12 and 14 positioned near each other. In this arrangement, the abdominal splinting device 10 provides support for the pregnant woman's back and abdomen by providing a gentle upward lift of the abdomen and also by bringing the abdomen closer to the woman's spine. By bringing the abdomen closer to the woman's spine, pressure on the woman's back is reduced, and the abdomen is also stabilized. The support and stabilization of the abdomen increases the pregnant woman's comfort, and allows the pregnant woman continue a free range of movement and exercise throughout the pregnancy. A further benefit of wearing the abdominal splinting device 10 in this position is that it causes a translational movement of the fetus within the woman's abdomen, moving the fetus closer to the woman's spine as well, relieving some of the pressure on the pregnant woman's bladder.

FIG. 5 shows the abdominal splinting device 10 worn by a pregnant woman in a second arrangement in accordance with the method of placement described above. As shown here, the abdominal splinting device 10 is worn with arms 12 and 14 positioned apart from each other, with first arm 12 positioned at or above the belly button, and second arm 14 positioned below the belly button. In addition to supporting the back and lifting the abdomen, this position also helps to further stabilize the abdomen. A benefit of wearing the abdominal splinting device 10 in this position is it increases the pregnant woman's comfort while moving and may encourage the pregnant woman to continue with her exercise routine.

Turning now to FIG. 6, the abdominal splinting device 10 is also designed to be worn by postnatal women. When worn by postnatal women, a benefit of wearing the abdominal splinting device 10 is that if the rectus abdominis has previously been separated as in the case of diastasis recti, the rectus abdominis halves are manually positioned near each other. The nearness of the muscle halves will facilitate healing of the diastasis recti by bringing the rectus abdominis halves in proximity to the midline of the woman's body so that the two halves may more easily reconnect during the healing process. In this embodiment, the abdominal splinting device 10 is designed to be worn during therapy to treat a diastasis recti and to further encourage healing. Healing is encouraged because the halves of the rectus abdominis muscle are brought into the proper position near the midline and the halves are protected from further separation by additional stretching of the muscle.

The abdominal splinting device 10 is worn by postnatal women in a similar way as by pregnant women. As before, the woman positions the back support panel on her torso. However, before crossing the arms 12 and 14 of the abdominal splinting device over her body as before, the postnatal woman may first manually position the halves of the rectus abdominis muscle near each other. The severity of a diastasis recti is measured by the number of finger widths a woman is able to insert into the diastasis when flexing the rectus abdominis. For the purposes of this invention, the halves of the rectus abdominis muscle shall be positioned near each other when the gap between the halves of the rectus abdominis muscle is reduced by at least one half finger width. Further, to ensure proper placement, the woman may choose to adjust the rectus abdominis muscle after the attachment mechanism 20 on arms 12 and 14 have been affixed to the mating zone 22.

The abdominal splinting device may be used in a therapeutic method of treating diastasis recti. In this method, the postnatal user will position the abdominal splinting device about her torso as previously described. Then, the user will perform therapeutic, abdominal strengthening exercises. For the purposes of this invention, abdominal strengthening exercises may mean transverse abdominal exercises and integrated core exercises, for example, vacuum exercises, ab sets, ab set variations, heel slides, dead bug exercises, heel taps, planks, and plank variations. Other transverse abdominal exercises and integrated core exercises known to practitioners in the art to engage the transverse abdominis muscle may be used without departing from the spirit of the invention.

When worn for therapeutic purposes as described previously, the benefit of the abdominal splinting device 10 is that it provides even traction and pressure from both sides of the separation, moving the rectus abdominis halves closer together and aligning them near the midline of the body.

Although the embodiments of the abdominal splinting device 10 pictured in the figures are directed to an abdominal splint for pregnant and postnatal women, the abdominal splinting device 10 may be used for other therapeutic procedures. For example, if a muscle or muscle group has been similarly stretched and weakened, the abdominal splinting device 10 of the present invention could be scaled to the appropriate size for therapeutic use.

As described, the abdominal splinting device 10 of the present invention provides many benefits. First, the abdominal splinting device 10 of the subject invention allows the user to position the arms 12 and 14 of the abdominal splinting device 10 about her body and onto mating zones 22 of the back support panel 11 of the abdominal splinting device 10 without additional help. Second, the abdominal splinting device 10 of the subject invention allows the user to position the arms 12 and 14 at the same time, instead of positioning first one arm and then another arm, thereby providing even traction across the diastasis. Third, when affixed to mating zones 22, the arms 12 and 14 of the abdominal splinting device 10 may be positioned without overlap, increasing the user's comfort while wearing the device. Fourth, the arms 12 and 14 of the abdominal splinting device 10 may worn near each other or separated from each other so that the user may provide a customized level of support and stabilization. Finally, because the abdominal splinting device 10 is fully adjustable, it may be worn by a woman both during her pregnancy and postpartum.

The foregoing provides a description of a abdominal splinting device 10, a description of how the corresponding abdominal splinting device 10 is arranged, and how the corresponding splinting device is used. However, this description illustrates only the principles of the invention. Since modification and change will readily occur, it is not desired to limit the invention to the exact construction and operation shown and described herein. Accordingly, all suitable modifications and equivalents are within the scope of this invention.

Although the present invention has been described above in detail, the same is by way of illustration and example only and is not to be taken as a limitation on the present invention.

I claim:

1. An abdominal splinting device, comprising:
a back support panel having an inner and outer surface, a central region and opposing first and second side regions;
a first arm extending outward from the first side region and a second arm extending outward from the second side region, each arm having a width less than any width of the back support panel and further having a length sufficient to contact the opposing side region, wherein the back support panel and each arm are comprised of a continuous elastic material;
each first and second side region having a mating zone located on the outer surface of the back support panel for receiving each arm extending from the opposing side region when the abdominal splinting device is wrapped around a human's trunk region;
each arm having a fastening system adapted to attach to the opposing side region mating zone; and
a length of non-slip material which extends from the first arm at a location beyond a periphery of the first side region onto and substantially across a longitudinal length of the back support panel inner surface onto the second arm to a location beyond a periphery of the second side region, said length of non-slip material having a portion located, on said first or second arm with a width less than any width of the first arm and second arm, and said length of non-slip material having a portion located on the back support panel with a width less than any width of said back support panel.

2. The abdominal splinting device of claim 1, wherein:
said length of non-slip material is comprised of multiple pieces of non-slip material.

3. The abdominal splinting device of claim 2, wherein:
said multiple pieces of non-slip material are in a linear arrangement.

4. The abdominal splinting device of claim 1, wherein:
multiple arms extend from the first side region.

5. The abdominal splinting device of claim 4, wherein:
multiple arms extend from the first side region and second side region.

6. The abdominal splinting device of claim 1, wherein:
the back support panel and the first and second arms are at least partially comprised of a cotton material.

7. The abdominal splinting device of claim 1, wherein:
the non-slip material as recited extends across a substantial longitudinal length of at least one arm.

8. The abdominal splinting device of claim 1, wherein:
the non-slip material as recited extends across a substantial longitudinal length of both arms.

9. The abdominal splinting device of claim 1, wherein:
The fastening system is selected from the group consisting of hook and loop closures, hook and eye closures, button closures, snap closures, and adhesives.

10. An abdominal splinting device, comprising:
a back support panel having an inner and outer surface, a central region and opposing first and second side regions;
a first arm extending outward from the first side region and a second arm extending outward from the second side region, each arm having a width less than any width of the back support panel and further having a length sufficient to contact the opposing, side region;
wherein the back support panel and each arm are comprised of a continuous elastic material;
each first and second side region having a mating zone located on the outer surface of the back support panel for receiving each arm extending from the opposing side region when the abdominal splinting device is wrapped around a human's trunk region;
each arm having an inner surface and terminating in a series of hooks attached to the inner surface; and
a length of non-slip material which extends from the first arm at a location beyond a periphery of the first side region onto and substantially across a longitudinal length of the back support panel onto the second arm to a location beyond a periphery of the second side region, said length of non-slip material having a portion located on said first or second arm with a width less than any width of the first arm and second arm, and said length of non-slip material having a portion located on the back support panel with a width less than any width of said back support panel.

11. The abdominal splinting device of claim 10, wherein:
multiple arms extend from the first side region.

12. The abdominal splinting device of claim 11, wherein:
multiple arms extend from the first side region and second side region.

13. The abdominal splinting device of claim 10, wherein:
the back support panel and the first and second arms are at least partially comprised of a cotton material.

14. The abdominal splinting device of claim 10, wherein: the non-slip material is attached to the inner surface of the back support panel.

15. The abdominal splinting device of claim 10, wherein: the non-slip material is attached to the inner surface of the arms.

16. The abdominal splinting device of claim 10, wherein: the mating zone is characterized by a series of loops to mate with the series of hooks.

17. A therapeutic method of treating diastasis recti, the method comprising the steps of:

providing an abdominal splinting device having inner and outer surfaces, a back support panel, first and second arms extending outward from each of first and second side regions of the back support panel, wherein the arms have a fastening system adapted to attach the arms to the back support panel affixed to the inner surface of the arms, the back support panel and each arm are comprised of a continuous elastic material; and a length of non-slip material which extends from the first arm substantially across a longitudinal length of the back support panel onto the second arm, said length of non-slip material having a portion located on said first or second arm with a width less than any width of the first arm and second arm, and said length of non-slip material having a portion located on the back support panel with a width less than any width of said back support panel;

centering the abdominal splinting device about a user's torso;

applying manual traction to the user's rectus abdominis to bring two opposing halves of the rectus abdominis near to each other;

crossing the first arm over the user's torso and affixing the first arm to the outer surface of the back support panel using an attaching means and simultaneously crossing the second arm over the user's torso and affixing the second arm to the outer surface of the back support panel using the attaching means; and instructing the user to perform abdominal strengthening exercises.

18. The therapeutic method of treating diastasis recti of claim 17, wherein: the fastening system is selected from the group consisting of hook and loop closures, hook and eye closures, button closures, snap closures, and adhesives.

19. The therapeutic method of treating diastasis recti of claim 17, wherein: the abdominal strengthening exercises are selected from the group consisting of transverse abdominal exercises and integrated core exercises.

\* \* \* \* \*